(12) United States Patent
Galfione

(10) Patent No.: US 9,161,845 B2
(45) Date of Patent: Oct. 20, 2015

(54) MACHINE FOR FORMING A CAST OF AN END PORTION OF AN AMPUTATED LIMB

(71) Applicant: Claudio Sarotto, Mondovi' (IT)

(72) Inventor: Silvio Galfione, Savigliano (IT)

(73) Assignees: Silvio Galfione, Savigliano (IT); Claudio Sarotto, Mondovr (IT)

( * ) Notice: Subject to any disclaimer, the term of this patent is extended or adjusted under 35 U.S.C. 154(b) by 0 days.

(21) Appl. No.: 14/384,448

(22) PCT Filed: Mar. 13, 2013

(86) PCT No.: PCT/IB2013/052001
§ 371 (c)(1),
(2) Date: Sep. 11, 2014

(87) PCT Pub. No.: WO2013/136284
PCT Pub. Date: Sep. 19, 2013

(65) Prior Publication Data
US 2015/0118338 A1    Apr. 30, 2015

(30) Foreign Application Priority Data

Mar. 13, 2012    (IT) .............................. TO2012A0217

(51) Int. Cl.
*A61F 2/80*    (2006.01)
*A61F 2/50*    (2006.01)
*A61F 2/60*    (2006.01)

(52) U.S. Cl.
CPC ................. *A61F 2/5046* (2013.01); *A61F 2/80* (2013.01); *A61F 2002/501* (2013.01); *A61F 2002/5021* (2013.01); *A61F 2002/5052* (2013.01); *A61F 2002/5053* (2013.01); *A61F 2002/607* (2013.01); *A61F 2240/004* (2013.01)

(58) Field of Classification Search
CPC ... A61F 2/5046; A61F 2/80; A61F 2240/004; A61F 2002/607; A61F 2002/5052; A61F 2002/5053; A61F 2002/501; A61F 2002/5021
USPC ............................................................ 425/2
See application file for complete search history.

(56) References Cited

U.S. PATENT DOCUMENTS

| 1,153,532 | A | * | 9/1915 | Apgar .......................... 12/146 M |
| 1,335,475 | A | * | 3/1920 | Bergman ....................... 264/222 |
| 2,424,278 | A | * | 7/1947 | Kunkel .......................... 264/222 |
| 2,488,922 | A | * | 11/1949 | Mead ............................ 264/571 |
| 5,503,543 | A | | 4/1996 | Laghi |
| 5,718,925 | A | * | 2/1998 | Kristinsson et al. .............. 425/2 |
| 5,885,509 | A | | 3/1999 | Kristinsson |
| 6,416,703 | B1 | | 7/2002 | Kristinsson et al. |
| 7,105,122 | B2 | * | 9/2006 | Karason ........................ 264/314 |
| 2004/0076700 | A1 | | 4/2004 | Horiguchi et al. |

FOREIGN PATENT DOCUMENTS

| GB | 2 232 598 | 12/1990 |
| WO | 95/05791 | 3/1995 |

* cited by examiner

*Primary Examiner* — Robert B Davis
(74) *Attorney, Agent, or Firm* — Greenblum & Bernstein P.L.C.

(57) ABSTRACT

A machine for forming a negative cast of an end portion of an amputated limb has an outer rigid tubular body; an elastically deformable tubular membrane housed within the rigid tubular body and having its opposite annular end portions fluid-tightly connected to the rigid tubular body, to define a through-duct through which the limb passes and, with the rigid tubular body, a fluid-tight elongated annular chamber with variable volume surrounding the limb; a reference membrane for positioning of the limb within the duct being provided at the outlet of the duct.

12 Claims, 6 Drawing Sheets

MACHINE FOR FORMING A CAST OF AN END PORTION OF AN AMPUTATED LIMB

TECHNICAL FIELD

The present invention concerns a machine for forming a cast of an end portion of an amputated limb.

BACKGROUND ART

In the field of the production of prostheses for amputated limbs, in particular lower limbs, to which the following discussion will explicitly refer without loss of generality, it is common practice to form a negative cast of the end portion or stump of the amputated limb, then, on the basis of said negative cast, produce a positive model, and form on the latter the attachment or socket portion of the respective prosthesis.

Currently, the negative cast is produced with the limb in a non weight-bearing condition, i.e. at rest. In order to obtain a model as close as possible to the end portion of the limb, the negative cast and/or the model subsequently produced undergo long, laborious and complex custom machining operations.

Once the attachment portion of the prosthesis has been formed based on the model, said attachment portion is customised by fitting it on the end portion of the patient's limb and performing a series of coupling tests in weight-bearing conditions. During these tests, the attachment portion is gradually modelled in order to eliminate localised stress on the limb and/or undesired deformation both of the muscular part and the soft tissues of the limb.

Although universally used, the procedure described not only requires great experience and sensitivity of the prosthetists, but also requires considerable time, entails a high level of patient involvement and essential cooperation of the patient.

DISCLOSURE OF INVENTION

The object of the present invention is to produce a machine for forming a cast of an end portion of an amputated limb, which solves the above-mentioned problems in a simple inexpensive manner and, in particular, allows the production of a final cast without the need for subsequent machining operations, at the same time reducing forming and customisation times.

According to the present invention a machine is produced for forming a cast of an end portion of an amputated limb, as claimed in claim 1.

BRIEF DESCRIPTION OF THE DRAWINGS

The invention will now be described with reference to the attached drawings, which illustrate some non-limiting embodiment examples, in which.

BEST MODE FOR CARRYING OUT THE INVENTION

Figure 1:
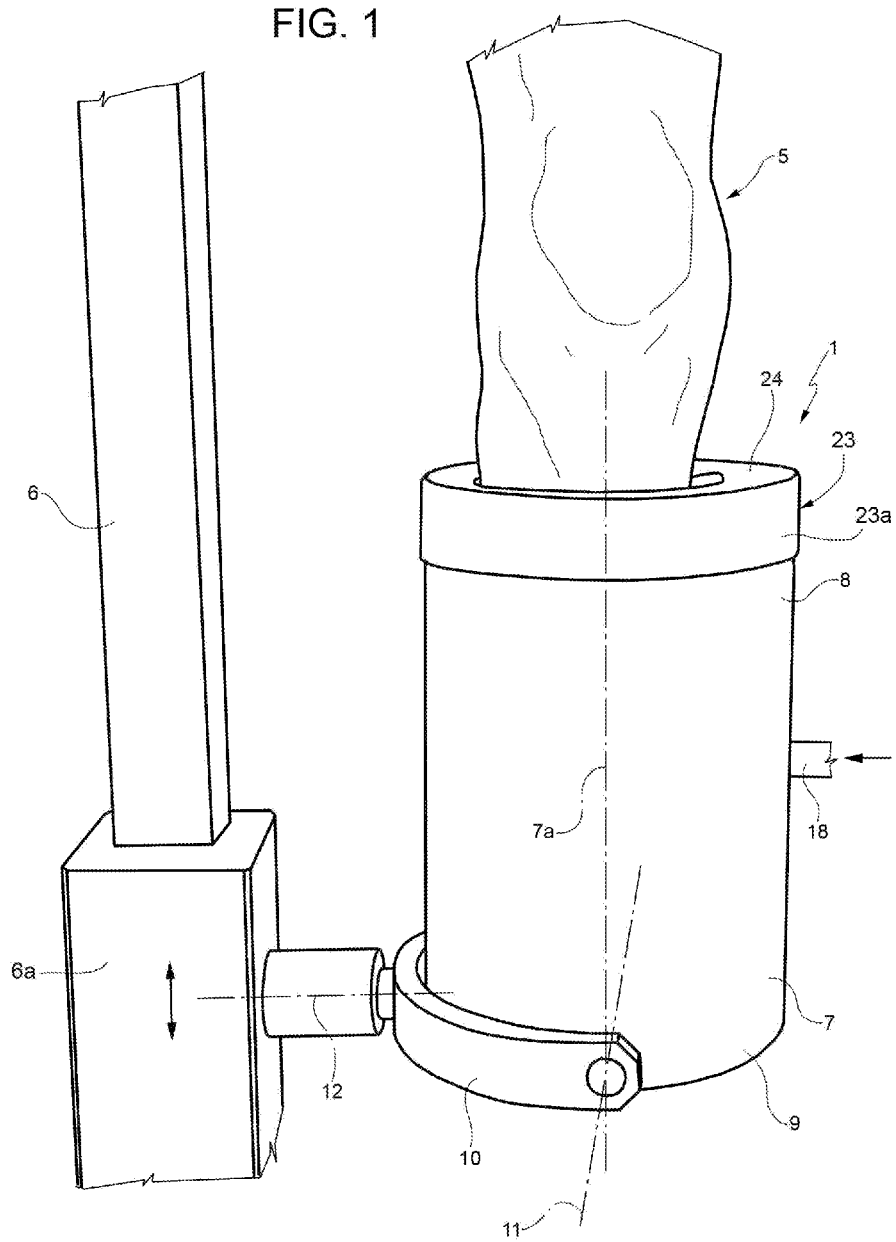
FIG. 1 illustrates, schematically and in side elevation, a preferred embodiment of a machine for forming a cast of an end portion of an amputated limb produced according to the teachings of the present invention.

In FIG. 1, the reference number 1 indicates, as a whole, a machine for forming a negative cast 2 (FIGS. 3 and 5) of an end portion 3 of an amputated limb 5.

The machine 1 comprises a fixed vertical upright 6, a slide 6a height-adjustable along the upright 6 and lockable in a fixed position along said upright 6 and a rigid cylindrical tubular body 7 having a substantially vertical axis 7a.

The tubular body 7 comprises an upper end portion 8 and a lower end portion 9, which is coupled to the arms of a fork-shaped body 10 to rotate around a horizontal axis 11. In turn, the fork-shaped body 10 is hinged to the slide to rotate around a horizontal axis 12 orthogonal to the axes 7a and 10.

Figure 2:
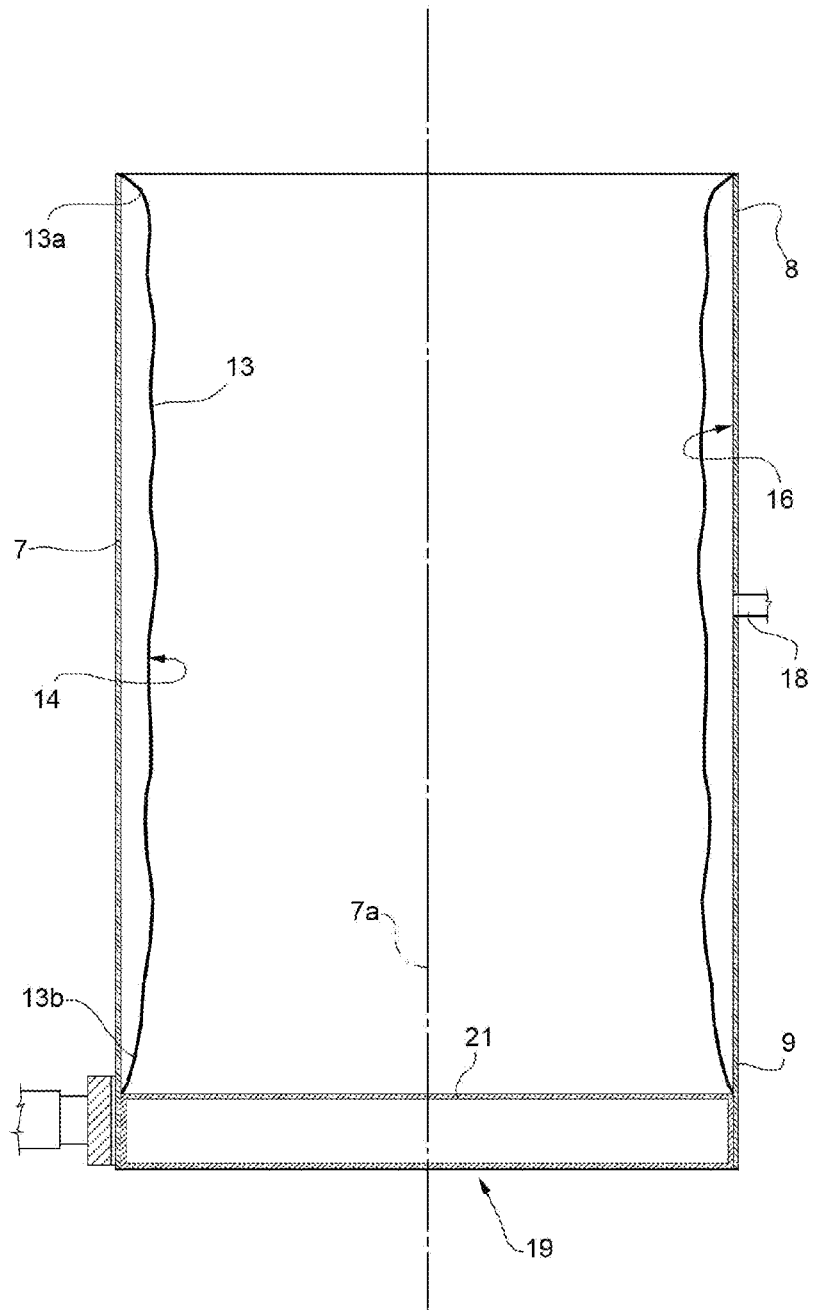
FIG. 2 illustrates schematically in section and on an enlarged scale, a detail of FIG. 1 in a rest condition.

With reference to FIG. 2, the machine 1 furthermore comprises an inner tubular membrane 13 made of elastically deformable material, for example a natural latex sheath. In the particular example described, the tubular membrane 13 conveniently has a thickness of approximately 1 mm and is housed within the rigid tubular body 7 along the axis 7a and has a generatrix which at rest is longer than the generatrix of said tubular body 7. The membrane 13 comprises opposite annular end portions, indicated by 13a and 13b fluid-tightly connected and in a per se known manner to the end portion 8 and, respectively, to the end portion 9 of the body 7 and delimits a through-duct 14 through which, in use, the portion 3 of the limb 5 passes. The membrane 13 delimits, with an inner surface of the rigid tubular body 7, a fluid-tight elongated annular chamber 16 having a variable volume, which surrounds the cast 2 (FIG. 3) and is pressurised by the introduction of a pressurised fluid, conveniently air, through an inlet valve 18.

Again with reference to FIGS. 2 and 3, the machine 1 furthermore comprises a axial reference compliant device 19 for a free end 3a of the portion 3 of the limb 5 protruding outside the channel 14. In the particular example described, the device 19 comprises an annular piston 20 housed within the portion 9 in an axially sliding manner, and a reference circular membrane 21, which is elastically compliant and stretched on the piston 20. The membrane 21 has vent holes adapted to allow the outflow of any air trapped inside the chamber 14 when the chamber 16 is pressurised and exerts a practically null force on the limb 3.

Again with reference to FIG. 1, the machine 1 furthermore comprises an annular cap 23 fitted on the portion 8 to define a stop for the section 13a of the membrane 13. The cap 23 comprises an attachment portion 23a and an elastic annular portion 24, protruding inside the tubular body 7 crosswise to the axis 7a and having a deformability under load lower than the deformability under load of the tubular membrane 13 with the function of axial containment of the membrane 13 when pressurised.

According to a variation not illustrated, the machine 1 is without the cap 23 and the membrane 13 deforms freely outside the portion 8 of the tubular body 7. The membrane 21 (FIG. 3) defines, on the opposite side of the tubular body 7, an axial stop for the portion 13b containing the membrane 13 when pressurised, analogous to the function performed by the annular portion 24.

Figure 4:
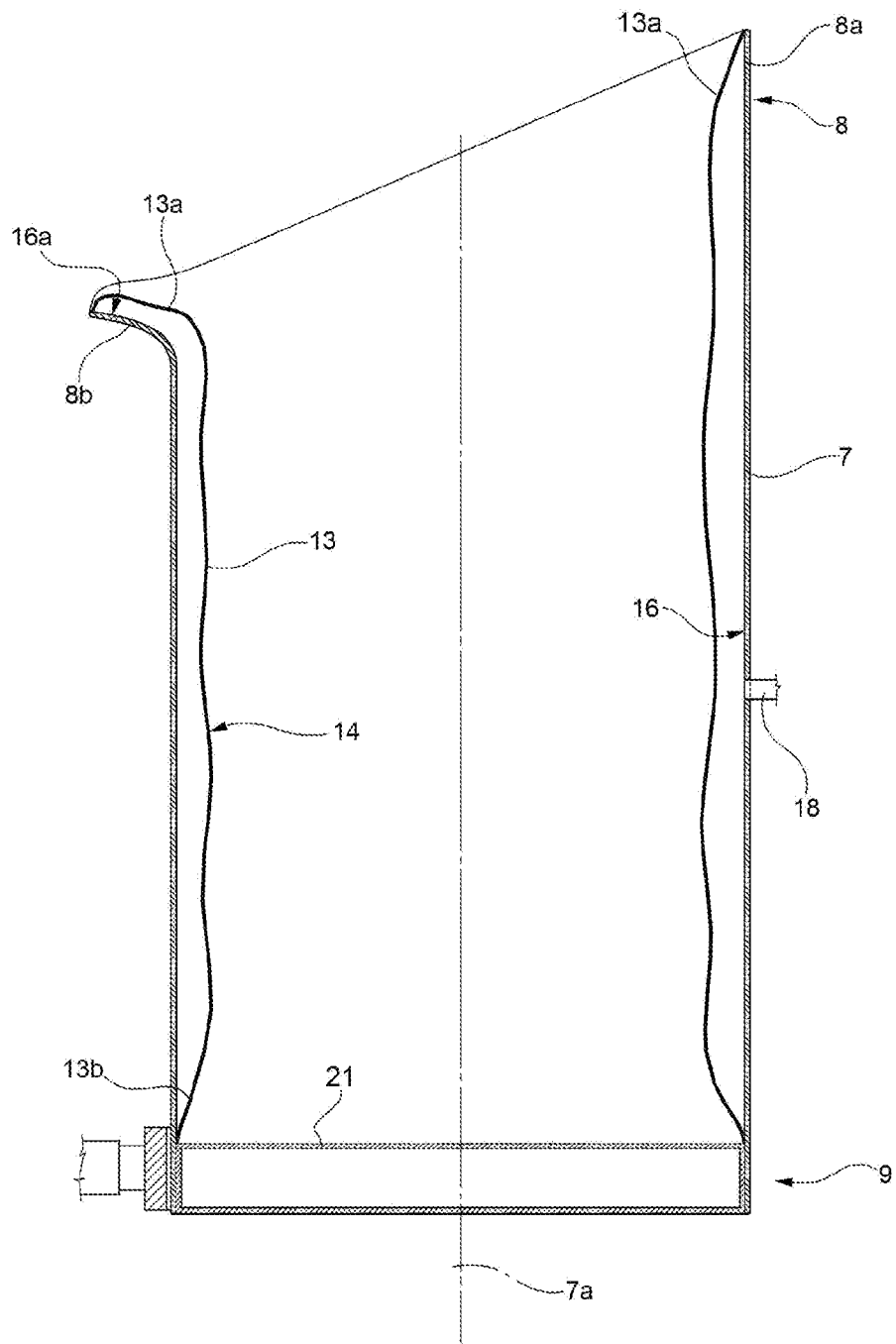
FIG. 4 illustrates, schematically and in section, a variation of a detail of FIG. 1 in a rest condition.
Figure 5:
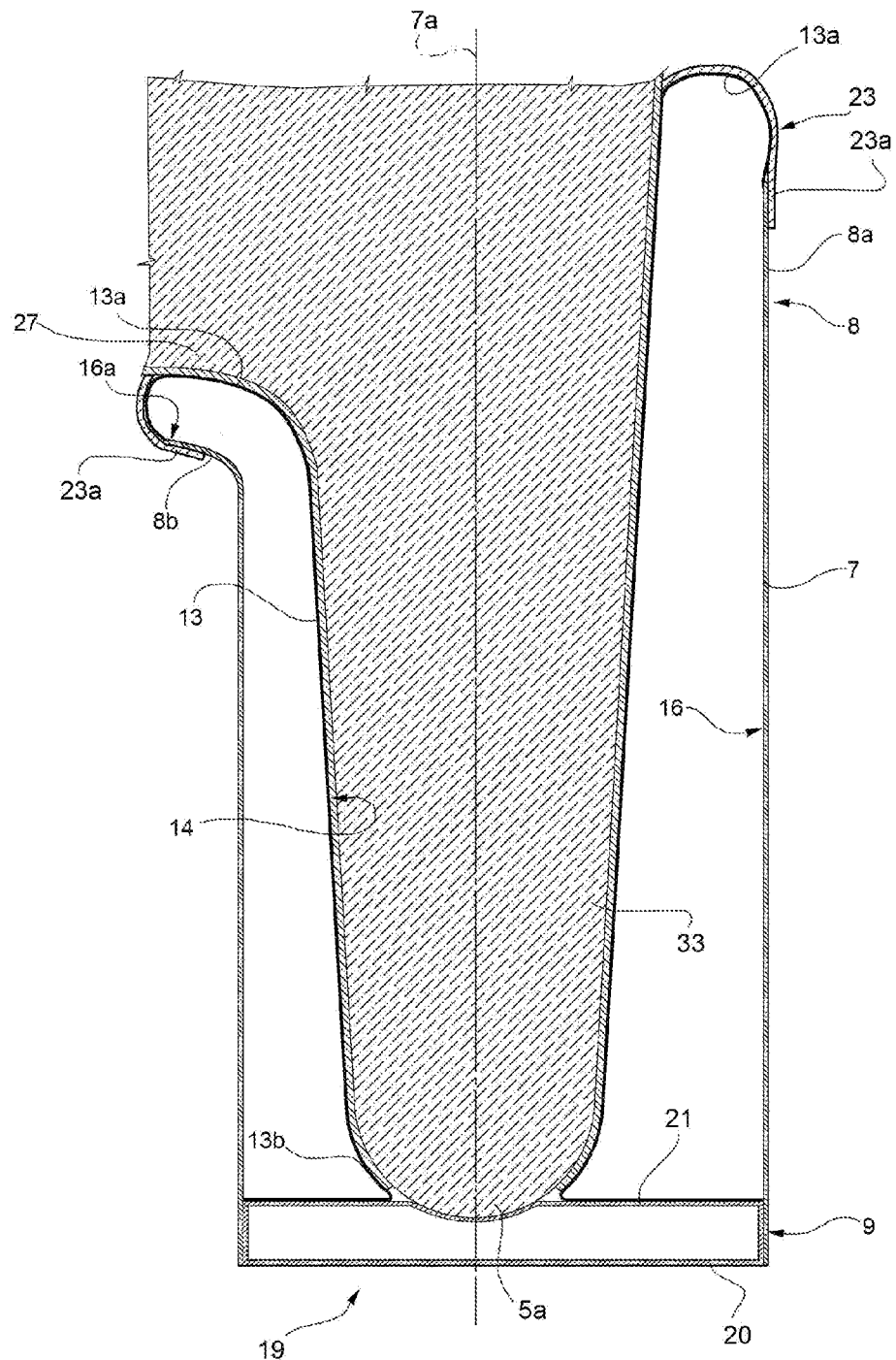
FIG. 5 is analogous to FIG. 4 and illustrates the detail of FIG. 4 in an operating condition.
Figure 6:
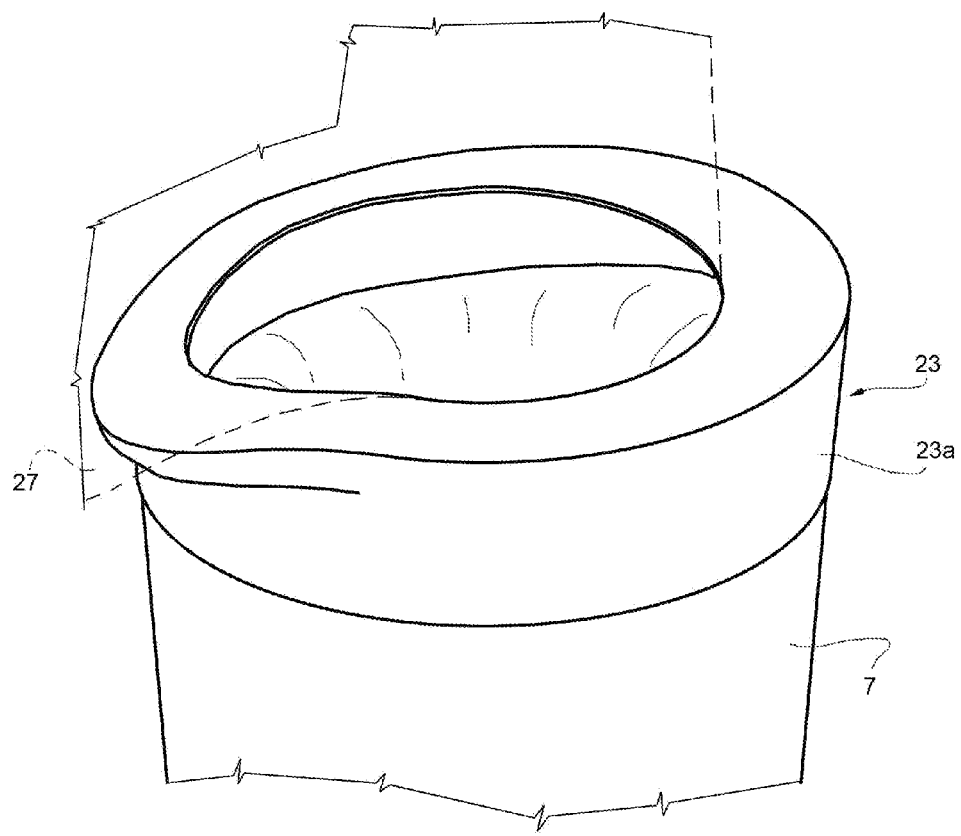
FIG. 6 illustrates a variation of a detail of FIG. 1.

In the variation illustrated in FIGS. 4, 5 and 6, the upper portion 8 of the tubular body 7 has an obliquely cut shape and comprises a section 8a with a substantially rectilinear generatrix and a diametrically opposite section 8b, folded outwards as a lip or half-saddle and lowered with respect to a free end edge of the section 8a. The section 8b is radiused to the section 8a and defines an accompaniment for an inguinal-ischial portion 27 of the patient. The membrane 13 delimits, with the portion 8a, an axial and lateral supporting cushion and with the folded portion 8b a part 16a of the variable volume chamber 16. The annular cap 23 is shaped to follow the cut and folded profile of the portion 8. The portion 16a defines, in use, an axial air cushion on which the inguinal-ischial portion 27 of the patient rests.

According to a variation not illustrated, the upper portion 8 is without the section 8a and comprises only the lip-shaped section 8b. Also in said solution the membrane 13, when pressurised, axially extends beyond the upper end edge of the portion 8a.

Figure 3:
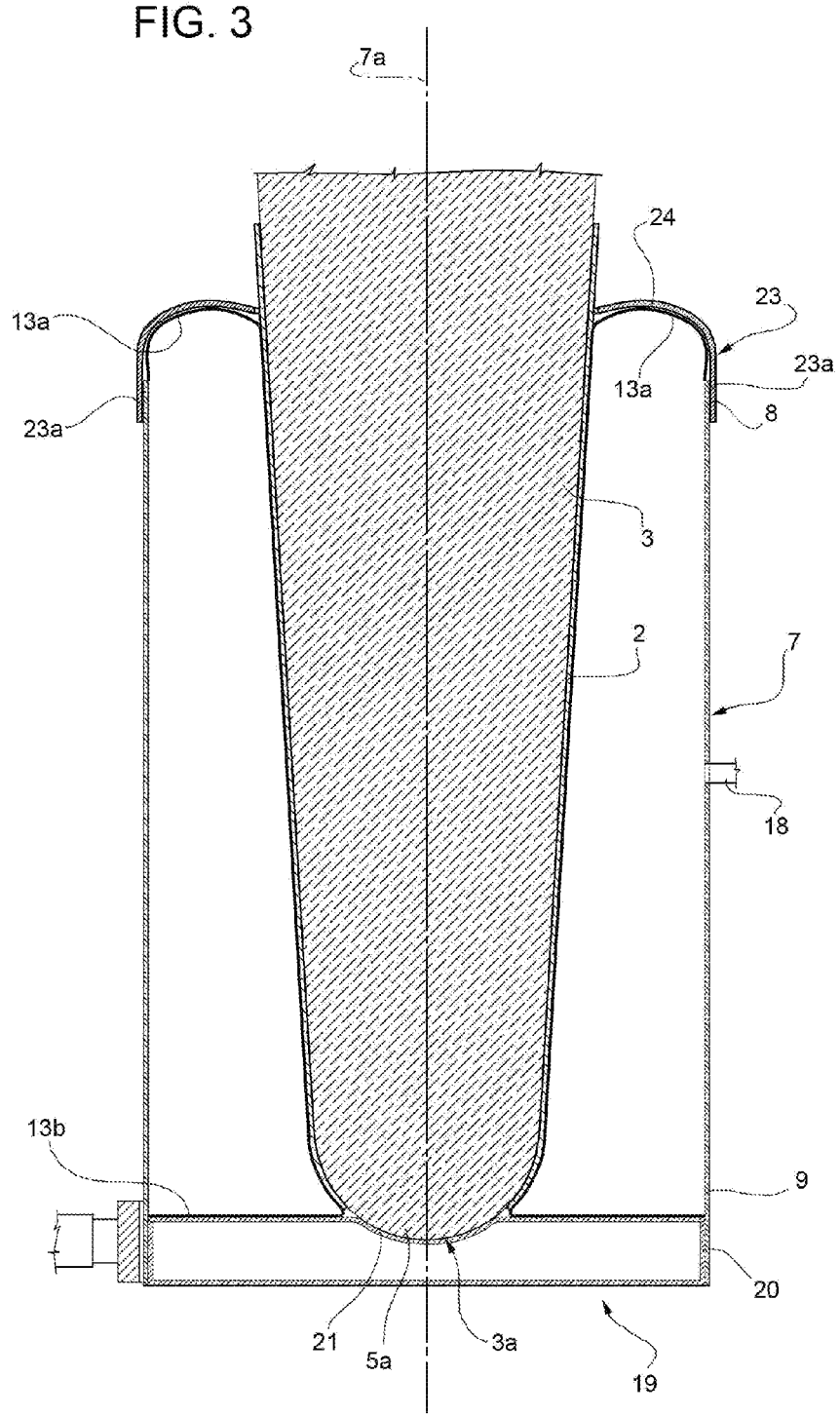
FIG. 3 illustrates, schematically and in section, a detail of FIG. 1 in a functional condition.

In use, with reference to FIGS. 1 and 3, in the specific case with tibial amputation, the end portion 3 of the limb 5, previously wrapped in a per se known manner in a plastically deformable bandage forming, once hardening is completed, the cast 2, is inserted in the channel 14 and moved forward until a distal end portion 5a of the limb 5 meets the membrane 21. At this point, the chamber 14 is progressively pressurised and consequently on the lateral surface of the portion 3 a force is exerted crosswise to the axis 7a which compresses and progressively sustains the limb 5 with respect to the tubular body 7. During pressurisation of the chamber 14, the patient progressively puts weight on the limb 5 until reaching a condition simulating weight supported on both feet. During this phase, due to the pressure exerted by the air, the bandage progressively deforms until it takes on a shape which is the exact negative of the form of the limb under load.

During the entire phase of production of the negative cast 2, the particular tubular shape of the membrane 13 and the presence of the membrane 21 inhibit the discharge of axial compression forces on the front surface 3a of the end portion of the limb 5. This avoids undesired swelling of the soft parts of the free end portion of the limb 5 and inhibits the formation of frontal or point loads on the bony part, since all the load reaction exercised by the patient is absorbed and countered solely by the actions exchanged between the lateral surface of the end portion 3 and the cast 2 which is being formed.

As can be seen from FIG. 3, during pressurisation of the chamber 14, the end portion 13a of the membrane 13 extends at the top outside the portion 8 of the tubular body, rests on the cap 23, when present, and, in any case, creates an annular cushion for the limb 5 which, in this way, is enveloped at least partially by the cushion, while the portion 13b is arranged to abut against the membrane 21. The above-mentioned cushion, arranged outside the upper end portion of the rigid tubular body 8, defines, in use, an axial and/or radial support for the limb 5.

The same forming operations described above are repeated also if the end portion 3 of the limb 5 is a femoral portion 33 (FIG. 5). In this case, the positions of the piston 20 and the membrane 21 are adjusted so that the inguinal and ischial portion 27 of the patient is arranged alongside the fold 8b. In this way, following application of the load and pressurisation of the chamber 16, the portion of bandage arranged near the ischial portion 27 is forced against the ischial portion and modelled exactly like the ischial portion 27. In this way, the subsequent socket will present an abutment for the ischial portion and the load will be discharged onto the prosthesis also via the abutment.

From the above, it is evident that the machine 1 described allows, on the one hand, modelling of the negative cast under load and, on the other, the production of negative casts and therefore positive models and corresponding finished sockets, i.e. which no longer require substantial machining adaptation operations.

The invention claimed is:

1. A machine for forming a negative cast of an end portion of an amputated limb, the machine comprising an outer rigid tubular body having a substantially vertical axis; an elastically deformable tubular membrane housed within said rigid tubular body along said axis; said membrane comprising opposite annular end portions fluid-tightly connected to corresponding opposite end portions of said rigid tubular body so as to define a through-duct through which said limb passes and, with the rigid tubular body, a fluid-tight elongated annular chamber having a variable volume surrounding the limb; the machine also comprising inlet means for an operative fluid for pressurising said chamber, and axial reference compliant means for a free end of said limb; said membrane, when deformed by the pressurised fluid, having at least one portion protruding outside said outer rigid tubular body and enveloping said limb at least partially.

2. The machine according to claim 1, characterised in that said portion protruding outside said tubular body defines a supporting cushion for said limb and arranged outside the upper end portion of said rigid tubular body.

3. The machine according to claim 1, characterised in that said reference compliant means have an adjustable position along the axis of said outer rigid tubular body.

4. The machine according to claim 3, characterised in that said reference compliant means comprise a flat membrane.

5. The machine according to claim 4, characterised in that said reference compliant means also comprise a piston annular body movable along said axis and holding said membrane stretched.

6. The machine according to claim 1, characterised by further comprising elastic stop means of said inner elastic membrane associated to said opposite end portions of said outer tubular body.

7. The machine according to claim 6, characterised in that said elastic stop means comprise an annular elastic membrane projecting within said tubular body from the top end portion of said tubular body and having a deformability under load lower than the deformability under load of said tubular membrane.

8. The machine according to claim 1, characterised in that said compliant support means form part of said elastic stop means.

9. The machine according to claim 1, characterised in that said top end portion comprises an end portion with lip folded outwards; said lip end portion defining a support for an ischial portion of the patient; said membrane defining, with said lip end portion, a part of said variable volume chamber.

10. The machine according to claim 9, characterised in that said membrane delimits, with said lip end portion, an axial supporting cushion for said ischial portion of the patient.

11. The machine according to claim 9, characterised in that said upper end portion comprises an end portion with a substantially rectilinear generatrix and diametrically opposite with respect to said lip end portion; said lip end portion being lower with respect to a free end edge of said end portion with a substantially rectilinear generatrix.

12. The machine according to claim 1, characterised in that said membrane has a generatrix longer than the generatrix of said outer rigid tubular body.

* * * * *

UNITED STATES PATENT AND TRADEMARK OFFICE
CERTIFICATE OF CORRECTION

PATENT NO.       : 9,161,845 B2
APPLICATION NO.  : 14/384448
DATED            : October 20, 2015
INVENTOR(S)      : Silvio Galfione Page 1 of 1

It is certified that error appears in the above-identified patent and that said Letters Patent is hereby corrected as shown below:

On the Title Page, at Item (71) should read as follows:
   --Applicants:   Silvio Galfione, Savigliano (IT)
                   Claudio Sarotto, Mondovi' (IT)--

On the Title Page, at Item (73) Assignees, of the printed patent, "Claudio Sarotto, Mondovr (IT)" should read --Claudio Sarotto, Mondovi' (IT)--

Signed and Sealed this
Sixteenth Day of August, 2016

Michelle K. Lee
*Director of the United States Patent and Trademark Office*